United States Patent [19]
Huffman et al.

[11] Patent Number: 6,063,950
[45] Date of Patent: May 16, 2000

[54] PROCESS FOR THE PREPARATION OF TITANOCENE DICHLORIDE

[75] Inventors: Mark Huffman, Edgewater; Joseph Payack, Somerset, both of N.J.

[73] Assignee: Merck & Co., Inc., Rahway, N.J.

[21] Appl. No.: 09/429,744

[22] Filed: Oct. 28, 1999

Related U.S. Application Data

[60] Provisional application No. 60/105,955, Oct. 28, 1998.
[51] Int. Cl.[7] .................................................. C07F 13/00
[52] U.S. Cl. ................................................................. 556/53
[58] Field of Search ................................................. 556/53

[56] References Cited

U.S. PATENT DOCUMENTS 5,847,176  12/1998  Sullivan .............................. 556/53 X
5,892,082   4/1999  Cai et al. ............................... 556/53

*Primary Examiner*—Paul F. Shaver
*Attorney, Agent, or Firm*—J. Eric Thies; David L. Rose

[57] ABSTRACT

The present invention is directed to a process for the preparation of titanocene dichloride ($Cp_2TiCl_2$) from the titanocene dimer ($Cp_2TiMe)_2O$), which is produced as a by-product from employing the reagent dimethyl titanocene ($Cp_2Ti(CH_3)_2$) in the methylenation of carbonyl compounds, such as esters and lactones.

14 Claims, No Drawings

PROCESS FOR THE PREPARATION OF TITANOCENE DICHLORIDE

This application claims priority from U.S. Ser. No. 60/105,955, filed Oct. 28, 1998.

BACKGROUND OF THE INVENTION

Titanocene dichloride is a valuable reagent for inorganic and organic chemistry. For example, titanocene dichloride is employed in the preparation of dimethyl titanocene (U.S. Pat. No. 5,892,082; PCT Patent Publication WO 97/09336) which is an effective methylenating reagent for a variety of carbonyl compounds, including esters and lactones (N. A. Petasis and E. I. Bzowej, *J. Am. Chem. Soc.*, 112, 6392–6394 (1990); U.S. Pat. No. 5,087,790). It is well recognized in the art that dimethyl titanocene has become a useful synthetic tool. See for example the extensive use of dimethyl titanocene by e.g., N. A. Petasis and M. A. Patane, *Tetrahedron Lett.*, 31, 6799 (1990); P. DeShong and P. J. Rybczynski, *J. Org. Chem.*, 56, 3207 (1991); J. S. Swenton, D. Bradin, B. D. Gates, *J. Org. Chem.*, 56, 6156 (1991); N. A. Petasis and E. I. Bzowej, *Tetrahedron Lett.*, 34, 1721 (1993); H. K. Chenault and L. F. Chafin, *J. Org. Chem.*, 59, 6167 (1994); D. Kuzmich, S. C. Wu, D.-C. Ha, C.-S. Lee, S. Ramesh, S. Atarashi, J.-K. Choi and D. J. Hart, *J Am. Chem. Soc.*, 116, 6943 (1994).

In conducting such methylenating reactions a stochiometric amount of dimethyl titanocene is employed, thereby requiring the purchase of stochiometric amounts of titanocene dicloride to prepare the dimethyl titanocene. Furthermore, a by-product of methylenating carbonyl compounds, such as esters and lactones, with dimethyl titanocene is the titanocene dimer $(Cp_2Ti(CH_3))_2O$ for which proper disposal must be arranged.

Accordingly, there is a need in the art for a more economical and efficient method for the preparation of titanocene dichloride. The present invention provides a more economical method for the preparation of titanocene dichloride in high yield from dimethyl titanocene dimer $(Cp_2Ti(CH_3))_2O$ and hydrogen chloride. The present process is readily amenable to the recycling of titanocene dichloride on a large scale.

SUMMARY OF THE INVENTION

The present invention is directed to a process for the preparation of titanocene dichloride $(Cp_2TiCl_2)$, a reagent which is useful in synthetic chemistry. In particular, the present invention is directed to a process for the preparation of titanocene dichloride $(Cp_2TiCl_2)$ from the titanocene dimer $(Cp_2Ti(CH_3))_2O$ (or "$(Cp_2TiMe)_2O$"), which is produced as a by-product from employing the reagent dimethyl titanocene $(Cp_2Ti(CH_3)_2)$ in methylenation reactions.

DETAILED DESCRIPTION OF THE INVENTION

The present invention is directed to processes for the conversion of $(Cp_2Ti(CH_3))_2O$ to $Cp_2TiCl_2$. In a preferred embodiment, the present invention is directed to a process for the preparation of titanocene dichloride $(Cp_2TiCl_2)$ from the dimethyl titanocene dimer $(Cp_2Ti(CH_3))_2O$ and hydrogen chloride. In a more preferred emdodiment, the hydrogen chloride is introduced as hydrogen chloride gas.

In one embodiment, this invention is directed to a process for the preparation of titanocene dichloride which comprises:

reacting titanocene dimer $(Cp_2Ti(CH_3))_2O$ with hydrogen chloride in a reaction mixture which comprises an organic solvent.

In a preferred embodiment, the hydrogen chloride is in the form of hydrogen chloride gas.

In a preferred embodiment, the organic solvent is tetrahydrofuran (THF), diethyl ether or toluene. In a more preferred embodiment, the organic solvent is tetrahydrofuran.

In a preferred embodiment, a solution of titanocene dimer in tetrahydrofuran is filtered to remove insoluble material prior to reacting with hydrogen chloride.

The conversion of $(Cp_2TiMe)_2O$ to $Cp_2TiCl_2$ occurs readily upon treatment with hydrogen chloride in an organic solvent. This can be accomplished by introducing hydrogen chloride gas into a solution or suspension of $(Cp_2TiMe)_2O$ in an organic solvent, preferably tetrahydrofuran or toluene. The use of tetrahydrofuran has the advantage of producing a more crystalline product which is easier to isolate by filtration and safer to handle as a dry solid. Tetrahydrofuran also allows for ambient temperature filtration of the solution of $(Cp_2TiMe)_2O$ to remove insoluble material prior to reaction with hydrogen chloride.

The metlhylenation of carbonyl groups may be conducted using dimethyltitanocene, $Cp_2Ti(CH_3)_2$, which is prepared from commercially available titanocene dichloride, $Cp_2TiCl_2$. The titanium byproduct of methylenation reactions which employ dimethyl titanocene $(Cp_2Ti(CH_3)_2)$ is the titanocene dimer $(Cp_2Ti(CH_3))_2O$ (or "$(Cp_2TiMe)_2O$") which is recovered from the reaction mixture. In accordance with the present invention, the recovered dimer is converted back to titanocene dichloride which is re-used in the synthesis.

The titanocene dimer $(Cp_2TiMe)_2O$ is somewhat unstable upon storage, decomposing at a rate of about 10% per month at 21° C. When stored at –10° C., decomposition is less than 1% in six months. As a result of decomposition, samples of $(Cp_2TiMe)_2O$ contain varying amounts of insoluble material which can be removed by filtration.

The reaction of the titanocene dimer $(Cp_2TiMe)_2O$ with hydrogen chloride proceeds via intermediates which are identifiable by $^1H$ NMR. These are $Cp_2Ti(Cl)O(Me)TiCp_2$, $(Cp_2TiCl)_2O$, and $Cp_2Ti(Cl)Me$.

In the instant processes the organic solvent may be selected from the group consisting of: tetrahydrofuran; toluene; diethyl ether; xylene (including o-xylene, m-xylene, p-xylene, and mixtures thereof); benzene; petroleum ether; hexane; heptane; cumene; mesitylene; digylme (2-methoxyethyl ether); methyl-t-butyl ether; a chlorinated hydrocarbon such as dichloromethane, chloroforrn, carbon tetrachloride, dichloroethane, chlorobenzene, ortho-dichlorobenzene; and the like; and mixtures thereof. In a preferred embodiment, the organic solvent comprises an inert solvent selected from the group consisting of: tetrahydrofuran; toluene; diethyl ether; benzene; xylene; petroleum ether; hexane; heptane; cumene; mesitylene; digylme; methyl-t-butyl ether; and mixtures thereof. In a more preferred embodiment, the organic solvent comprises a solvent selected from the group consisting of: tetrahydrofuran; toluene; diethyl ether; methyl-t-butyl ether; xylene; benzene; and mixtures thereof. In an even more preferred embodiment, the organic solvent comprises a solvent which is selected from: tetrahydrofuran; toluene; and mixtures thereof. In a most preferred embodiment, the organic solvent comprises tetrahydrofuran or toluene. Other ingredients may be present in the reaction mixture, for example, to facilite the preparation of titanocene dichloride or to monitor the progress of the reaction.

The instant process may be conducted within a temperature range of between about −20 and about 25° C., wherein the more prefered temperature range is between about −10 and about 15° C. and the most preferred temperature range is between about −5 and about 10° C.

In the instant process the molar ratio of titanocene dimer to hydrogen chloride is typically in the range of from about 1:1 to about 6:1, preferably about 1:1 to about 5:1, and more preferably about 1:1 to about 4:1.

The starting material for the present process is titanocene dimer. "Titanocene dimer" is represented by the formula $(Cp_2Ti(CH_3))_2O$ (i.e. "$(Cp_2TiMe)_2O$"). Titanocene dimer is also called tetrakis($\eta^5$-cyclopenta-dienyl)dimethyl-$\mu$-oxo-dititanium and has the following chemical structure:

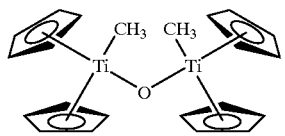

The product of the present process is titanocene dichloride. "Titanocene dichloride" is represented by the formula $Cp_2TiCl_2$ wherein "Cp" indicates the presence of a cyclopentadienyl (cyclopentadienylide) ("$C_5H_5$") group. Titanocene dichloride is also called di(cyclopentadienyl)-titanium dichloride or bis($\eta^5$-cyclopentadienyl)dichlorotitanium and has the following chemical structure:

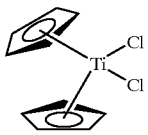

The preparation of the desired compound with the process of the present invention may be carried out in sequential or convergent synthetic routes. It is noted that in some cases the order of carrying out the subject reactions may be varied to facilitate the reaction or to avoid unwanted reaction products. In general, the process of the present invention is conducted in a sequential manner as presented herein.

NMR spectra were run in $CDCl_3$ and the $^1H$ and $^{13}C$ spectra were measured at 250 and 62.9 MHz. The proton spectra were run with a 10s delay between pulses for the wt % assay. Toluene was dried to less than 150 $\mu$g/mL water (by Karl Fisher titration) with 3 Å sieves. Standard inert atmosphere techniques were used for the reaction and work-up.

Many of the starting materials are either commercially available or known in the literature and others can be prepared following literature methods described for analogous compounds. The skills required in carrying Out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

| Materials | Amount |
|---|---|
| $(Cp_2TiMe)_2O$ (99 wt %) | 15.0 g, 36.9 mmol |
| HCl | >5.4 g, 148 mmol |
| Solka Floc | 1 g |
| Tetrahydrofuran | 100 mL |
| Heptane | 35 mL |

The titanium dimer $(Cp_2TiMe)_2O$ was dissolved in 75 mL of THF at ambient temperature. The solution was filtered through a pad of the filtration aid Solka Floc™ into a 250 mL 3-neck flask equipped with mechanical stirrer, HCl gas inlet, and an outlet to a trap filled with NaOH solution. The filter cake was washed with 10 mL THF. The solution was cooled in an ice-water bath and HCl gas was introduced above surface at a controlled rate (exotherm), keeping the batch temperature below 15° C. Note: HCl addition subsurface causes immediate precipitation which rapidly plugs the line in small scale equipment. During the addition, an orange suspension appeared as the intermediates precipitated. The suspension turned red as conversion to $Cp_2TiCl_2$ proceeded. When $^1H$ NMR indicated conversion was complete (<1% $Cp_2Ti(Cl)Me$), the excess HCl was flushed out with a nitrogen sweep. Heptane (28 mL) was added to the 0° C. suspension over 30 minutes. The mixture was then filtered, rinsing with 3:1 THF/heptane and the red-purple crystalline solid was dried under vacuum at 21° C. (Yield 17.2 g, 69.1 mmol, 94%).

$^1H$ NMR, 250 MHz, $CDCl_3$; all peaks are singlets

| | |
|---|---|
| $(Cp_2TiMe)_2O$ | 5.82 ppm (20 H), 0.52 (6 H) |
| $Cp_2TiCl_2$ | 6.59 (10 H) |
| $Cp_2Ti(Cl)Me$ | 6.27 (10 H), 0.80 (3 H) |
| $(Cp_2TiCl)_2O$ | 6.30 (20 H) |
| $Cp_2Ti(Cl)O(Me)TiCp_2$ | 6.14 (10 H), 5.98 (10 H), 0.67 (3 H) |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of titanocene dichloride which comprises:

reacting titanocene dimer $(Cp_2Ti(CH_3))_2O$ with hydrogen chloride in a reaction mixture which comprises an organic solvent.

2. The process of claim 1 wherein the reaction mixture comprises an organic solvent selected from the group consisting of:

tetrahydrofuran; diethyl ether; toluene; benzene; xylene; petroleum ether; hexane; heptane; cumene; mesitylene; digylme; methyl-t-butyl ether; and mixtures thereof.

3. The process of claim 2 wherein the organic solvent is selected from the group consisting of: tetrahydrofuran; diethyl ether; methyl-t-butyl ether; toluene; xylene; benzene; and mixtures thereof.

4. The process of claim 3 wherein the organic solvent comprises a solvent which is selected from: tetrahydrofuran; toluene; and mixtures thereof.

5. The process of claim 1 wherein the organic solvent comprises tetrahydrofuran.

6. The process of claim 1 wherein the organic solvent comprises toluene.

7. The process of claim 1 wherein the hydrogen chloride is in the form of hydrogen chloride gas.

8. The process of claim 1 wherein the temperature range is between about −20 and about 25° C.

9. The process of claim 8 wherein the temperature range is between about −10 and about 15° C.

10. The process of claim 9 wherein the temperature range is between about −5 and about 10° C.

11. The process of claim 1 wherein the molar ratio of titanocene dimer to hydrogen chloride is in the range of from about 1:1 to about 6:1.

12. The process of claim 11 wherein the molar ratio of titanocene dimer to hydrogen chloride is in the range of from about 1:1 to about 5:1.

13. The process of claim 12 wherein the molar ratio of titanocene dimer to hydrogen chloride is in the range of from about 1:1 to about 4:1.

14. A process for the preparation of titanocene dichloride which comprises:

reacting hydrogen chloride with titanocene dimer ($Cp_2Ti(CH_3)$)$_2O$ at a molar ratio of from about 1:1 to about 4:1 in a reaction mixture which comprises an organic solvent which is selected from: tetrahydrofuran; toluene; and mixtures thereof, at a temperature range of between about −10 and about 15° C.

* * * * *